United States Patent
Mou et al.

(10) Patent No.: US 10,955,319 B2
(45) Date of Patent: *Mar. 23, 2021

(54) GAS DETECTING DEVICE

(71) Applicant: Microjet Technology Co., Ltd., Hsinchu (TW)

(72) Inventors: Hao-Jan Mou, Hsinchu (TW); Chi-Feng Huang, Hsinchu (TW); Yung-Lung Han, Hsinchu (TW); Hsuan-Kai Chen, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 108 days.

This patent is subject to a terminal disclaimer.

(21) Appl. No.: 16/243,545

(22) Filed: Jan. 9, 2019

(65) Prior Publication Data
US 2019/0234839 A1 Aug. 1, 2019

(30) Foreign Application Priority Data

Jan. 31, 2018 (TW) .................................. 107103541

(51) Int. Cl.
*G01N 33/00* (2006.01)
*G01N 1/22* (2006.01)
(52) U.S. Cl.
CPC ......... *G01N 1/2273* (2013.01); *G01N 33/004* (2013.01); *G01N 33/0022* (2013.01); *G01N 33/0047* (2013.01)
(58) Field of Classification Search
CPC . G01N 1/2273; G01N 33/004; G01N 33/0047
See application file for complete search history.

(56) References Cited

U.S. PATENT DOCUMENTS

2010/0229658 A1* 9/2010 Glezer ................. G01N 1/2273
73/863.81
2014/0377099 A1* 12/2014 Hsueh .................... F04B 49/22
417/413.2
(Continued)

FOREIGN PATENT DOCUMENTS

CN 106233119 A 12/2016
TW 201530112 A 8/2015
(Continued)

*Primary Examiner* — Jamel E Williams
(74) *Attorney, Agent, or Firm* — Birch, Stewart, Kolasch & Birch, LLP

(57) ABSTRACT

A gas detecting device includes a casing, at least one gas transporting actuator, at least one valve and at least one external sensor. The casing has an airflow chamber, an inlet, a branch channel and a connection channel. The airflow chamber communicates with an environment outside the casing through the inlet, and the branch channel communicates with the airflow chamber and the connection channel. The gas transporting actuator is disposed on the branch channel for transporting air into the airflow chamber and the branch channel from the inlet and has a gas inlet plate, a resonance plate and a piezoelectric actuator. The valve is disposed between the connection channel and the branch channel for controlling the air to flow into the connection channel. The external sensor is detachably disposed in the connection channel and has a sensor for measuring the air in the connection channel.

11 Claims, 12 Drawing Sheets

(56) References Cited

U.S. PATENT DOCUMENTS

| | | | |
|---|---|---|---|
| 2016/0245714 A1 | 8/2016 | Gagne et al. | |
| 2019/0212242 A1* | 7/2019 | Mou | G01N 33/004 |
| 2019/0234838 A1* | 8/2019 | Mou | G01N 1/2273 |
| 2019/0234839 A1* | 8/2019 | Mou | G01N 1/2273 |
| 2019/0234840 A1* | 8/2019 | Mou | G01N 1/2273 |
| 2019/0265132 A1* | 8/2019 | Mou | G01N 33/0073 |

FOREIGN PATENT DOCUMENTS

| | | |
|---|---|---|
| TW | M553417 U | 12/2017 |
| TW | M554513 U | 1/2018 |

* cited by examiner

GAS DETECTING DEVICE

FIELD OF THE DISCLOSURE

The present disclosure relates to a gas detecting device, and more particularly to a gas detecting device having a gas transporting actuator for gas transportation.

BACKGROUND OF THE DISCLOSURE

Nowadays, the air pollution problems are becoming increasingly serious in our country and its neighboring regions. There are many harmful gases to human body in daily life. If it fails to be detected in time, it will affect the health of the human body.

Moreover, there are different demands of gas detection for users in different places (e.g., factories, offices or homes). For example, gas sensors for detecting volatile gases or toxic gases causing inhalation injuries are suitably used in factories. Carbon monoxide sensors, carbon dioxide sensors, temperature sensors or humidity sensors are suitably used in homes and offices. Since the commercially available gas detecting device is an integral gas detecting device, some drawbacks occur. For example, the type of the gas to be detected has been determined before the gas detecting device leaves the factory and cannot be changed by the users according to the particle requirements. In that, a gas detecting device cannot provide complete detections to meet the requirements of users. Therefore, there is a need of providing a gas detecting device capable of performing gas detection according to different requirements to address the above-mentioned issues.

SUMMARY OF THE DISCLOSURE

An object of the present disclosure is to provide a gas detecting device having an external sensor for detecting air and providing users with air information timely and accurately. The external sensor of the gas detecting device can be selected and matched according to the requirements of the users. It has benefits for achieving the purposes of easy replacement and improving practicality and convenience.

In accordance with an aspect of the present disclosure, a gas detecting device is provided. The gas detecting device includes a casing, at least one gas transporting actuator, at least one valve and at least one external sensor. The casing has an airflow chamber, at least one inlet, at least one branch channel and at least one connection channel. The airflow chamber is in fluid communication with an environment outside the casing through the at least one inlet, the at least one branch channel is in fluid communication with the airflow chamber, and the at least one connection channel is in fluid communication with the at least one branch channel. The at least one gas transporting actuator is disposed on the at least one branch channel, has a gas inlet plate, a resonance plate and a piezoelectric actuator, and is actuated to inhale air into the airflow chamber through the at least one inlet and transport the air into the at least one branch channel. The at least one valve is disposed between the at least one connection channel and the at least one branch channel to control the air to flow into the at least one connection channel. The at least one external sensor is detachably assembled in the at least one connection channel and includes a sensor to measure the air in the at least one connection channel.

The above contents of the present disclosure will become more readily apparent to those ordinarily skilled in the art after reviewing the following detailed description and accompanying drawings, in which:

DETAILED DESCRIPTION OF THE PREFERRED EMBODIMENT

Figure 1:
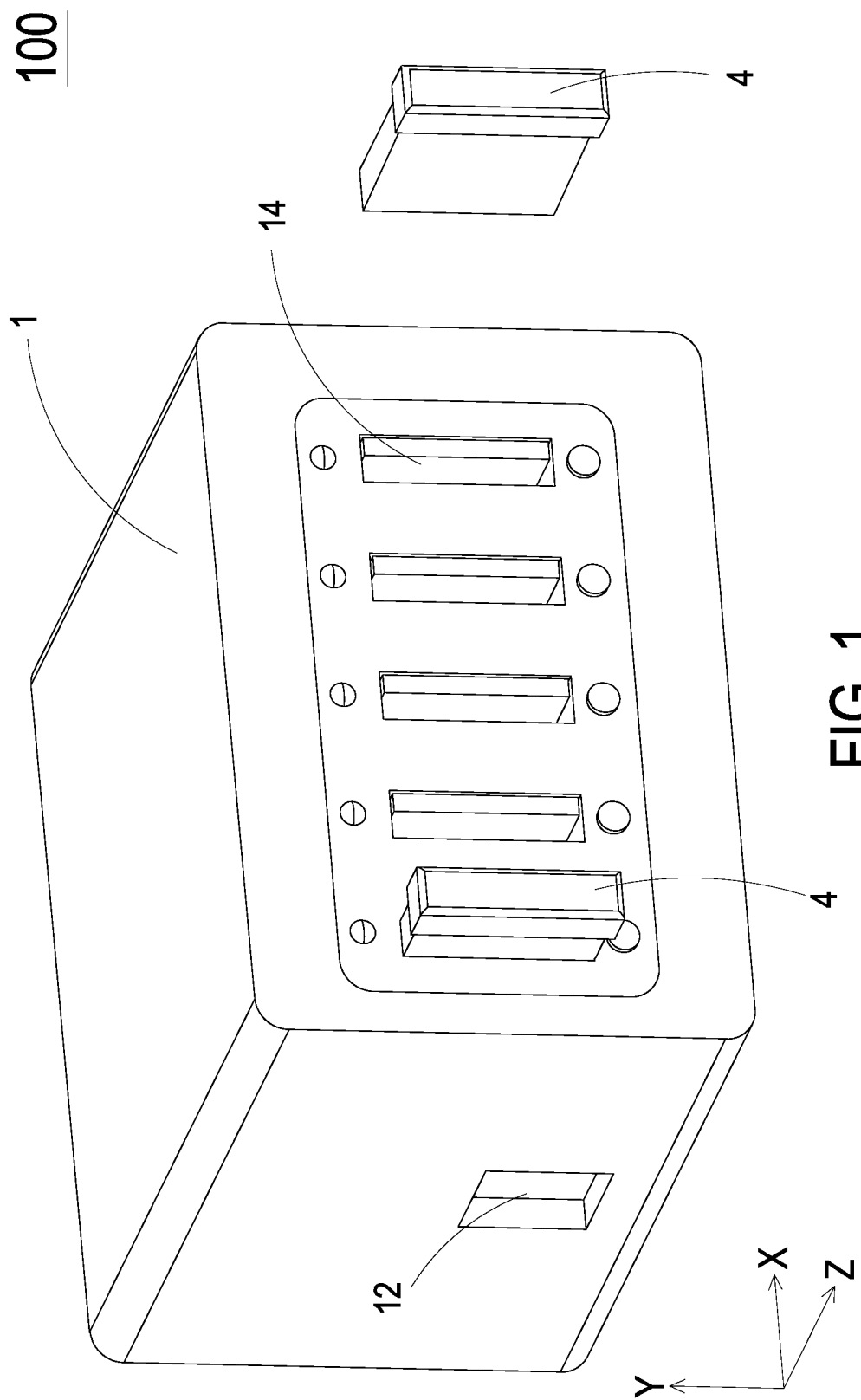
FIG. 1 is a schematic perspective view illustrating a gas detecting device according to an embodiment of the present disclosure.

The present disclosure will now be described more specifically with reference to the following embodiments. It is to be noted that the following descriptions of preferred embodiments of this disclosure are presented herein for purpose of illustration and description only. It is not intended to be exhaustive or to be limited to the precise form disclosed.

Please refer to FIGS. 1 to 4. The present disclosure provides a gas detecting device 100 including at least one casing 1, at least one gas transporting actuator 2, at least one valve 3, at least one external sensor 4, at least one airflow chamber 11, at least one inlet 12, at least one branch channel 13, at least one connection channel 14, at least one gas inlet plate 21, at least one resonance plate 22, at least one piezoelectric actuator 23 and at least one external sensor 4. The numbers of the casing 1, the airflow chamber 11, the gas inlet plate 21, the resonance plate 22, the piezoelectric actuator 23 and the external sensor 4 are exemplified by one for each respectively in the following embodiments but not limited thereto. It is noted that each of the casing 1, the airflow chamber 11, the gas inlet plate 21, the resonance plate 22, the piezoelectric actuator 23 and the external sensor 4 can also be provided in plural numbers.

Figure 2:
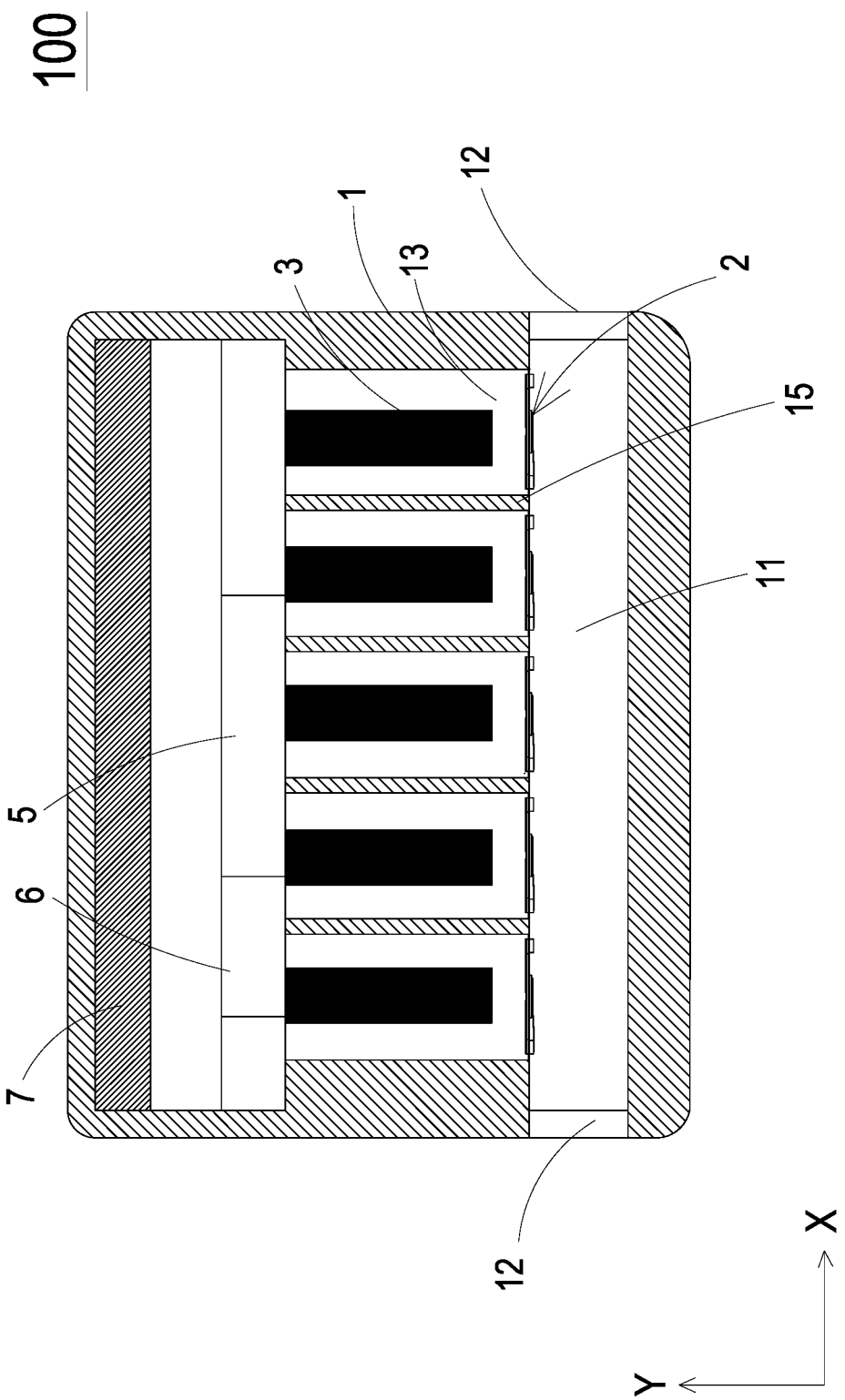
FIG. 2 is a schematic cross-sectional view illustrating the gas detecting device of FIG. 1.
Figure 3:
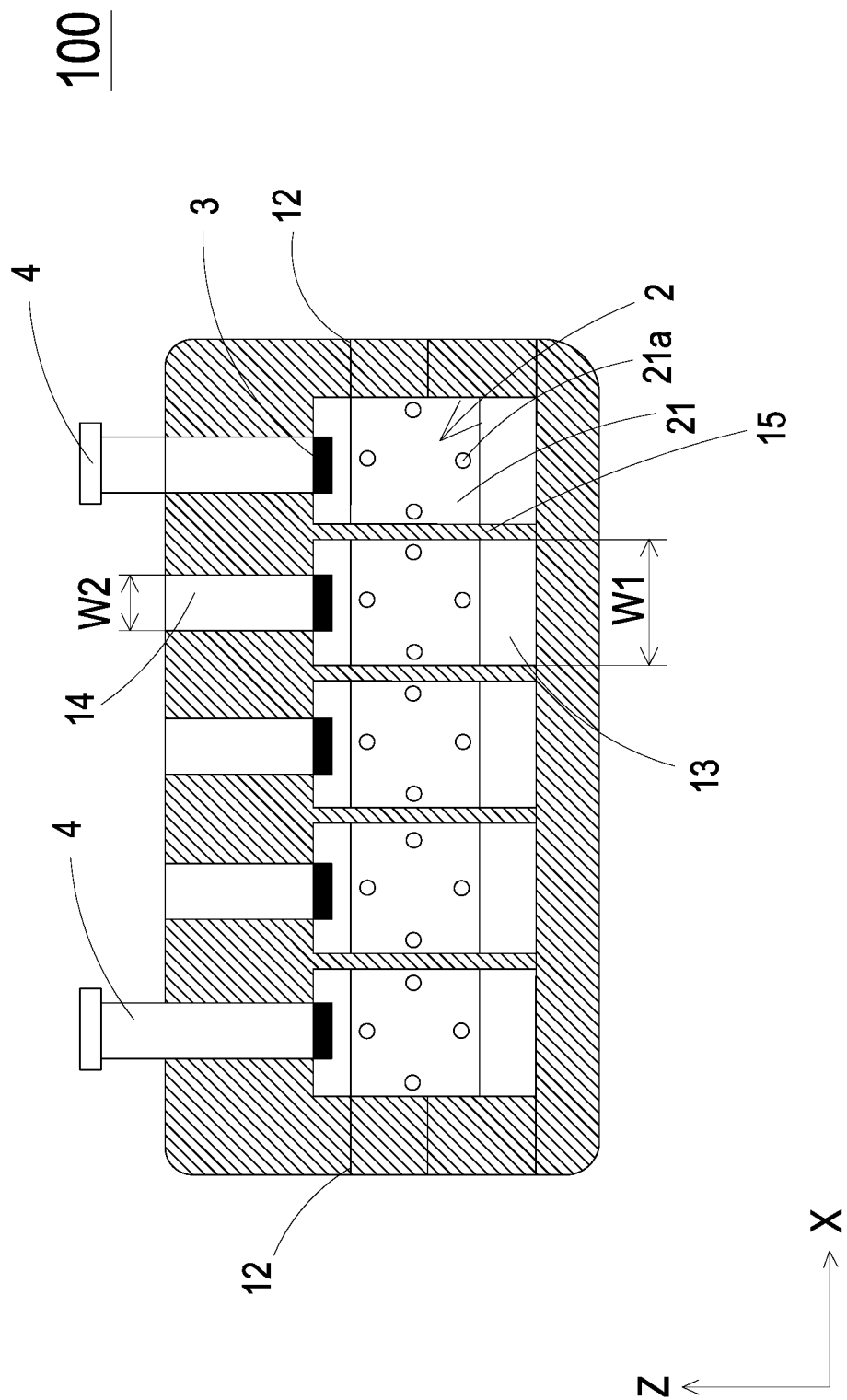
FIG. 3 is a schematic cross-sectional view illustrating a gas transporting actuator of a gas detecting device of the present disclosure.

The present disclosure provides a gas detecting device 100. Please refer to FIGS. 1 to 3. FIG. 1 is a three-dimensional view of the present disclosure. FIG. 2 is a sectional view taken in the X-Y plane, and FIG. 3 is a sectional view taken in the X-Z plane. In the embodiment, the gas detecting device 100 includes a casing 1, at least one gas transporting actuator 2, at least one valve 3 and at least one external sensor 4. The casing 1 has an airflow chamber 11, at least one inlet 12, at least one branch channel 13 and at least one connection channel 14. The numbers of the branch channels 13, the connection channels 14, the gas transporting actuators 2 and the valves 3 are corresponding to each other, respectively. The numbers of the branch channels 13, the connection channels 14, the gas transporting actuators 2 and the valves 3 are exemplified by five for each respectively in the following embodiments but not limited thereto. The airflow chamber 11 is in fluid communication with the environment outside the casing 1 through the at least one inlet 12 and is in fluid communication with the five branch channels 13. The casing 1 includes a plurality of partition plates 15 used to space apart the five branch channels 13 and the five connection channels 14. More specifically, the casing 1 has a convergence chamber disposed on the airflow chamber 11 along the Y-axis and extending beyond the airflow chamber 11 along the Z-axis. The partition plates 15 divides the convergence chamber into the five branch channels 13, and thus defines five parts, each of which consists of the branch channel 13 and the connection channel 14, separated from each other. The airflow chamber 11 extends along the X-axis and is exposed to the environment on both ends via the at least one inlet 12, and also connects to the five branch channels 13 along the Y-axis. The five connection channels 14 extend along the Z-axis to a side surface of the casing 1, and are open to the environment outside the casing 1. Moreover, the branch channel 13 has a width W1 and the connection channel 14 has a width W2 along the X-axis. The width W1 is greater than the width W2. The five connection channels 14 are corresponding in number and positions to and in fluid communication with the five branch channels 13. The five gas transporting actuators 2 are correspondingly disposed in the five branch channels 13, respectively, to transport air contained in the airflow chamber 11 into the corresponding branch channels 13. In some embodiments, the gas transporting actuator 2 may be placed more deeply in the branch channels 13 by adjusting its position along the Y-axis. The five valves 3 are correspondingly disposed between the five connection channels 14 and the five branch channels 13 to control the air to flow into the corresponding connection channels 14. The valve 3 is substantially perpendicular to the gas transporting actuators 2. The valve 3 extends along the Y-axis and seals the junction between the connection channel 14 and the branch channel 13, thereby controlling the air to be discharged into the corresponding connection channels 14. Moreover, the five external sensors 4 are detachably assembled in the five corresponding connection channels 14, respectively. Each external sensor 4 includes a sensor (not shown) disposed therein. In the embodiment, the sensor of the external sensor 4 can be at least one selected from the group consisting of an oxygen sensor, a carbon monoxide sensor, a carbon dioxide sensor and combinations thereof. In an embodiment, the sensor of the external sensor 4 can be a volatile organic compound sensor. Alternatively, the sensor of the external sensor 4 can be at least one selected from the group consisting of a bacterial sensor, a virus sensor, a microorganism sensor and combinations thereof. Alternatively, the sensor of the external sensor 4 can be at least one selected form the group consisting of a temperature sensor, a humidity sensor and combinations thereof. In that, the sensor of the external sensor 4 is used to measure the air contained in the connection channel 14.

Figure 4A:
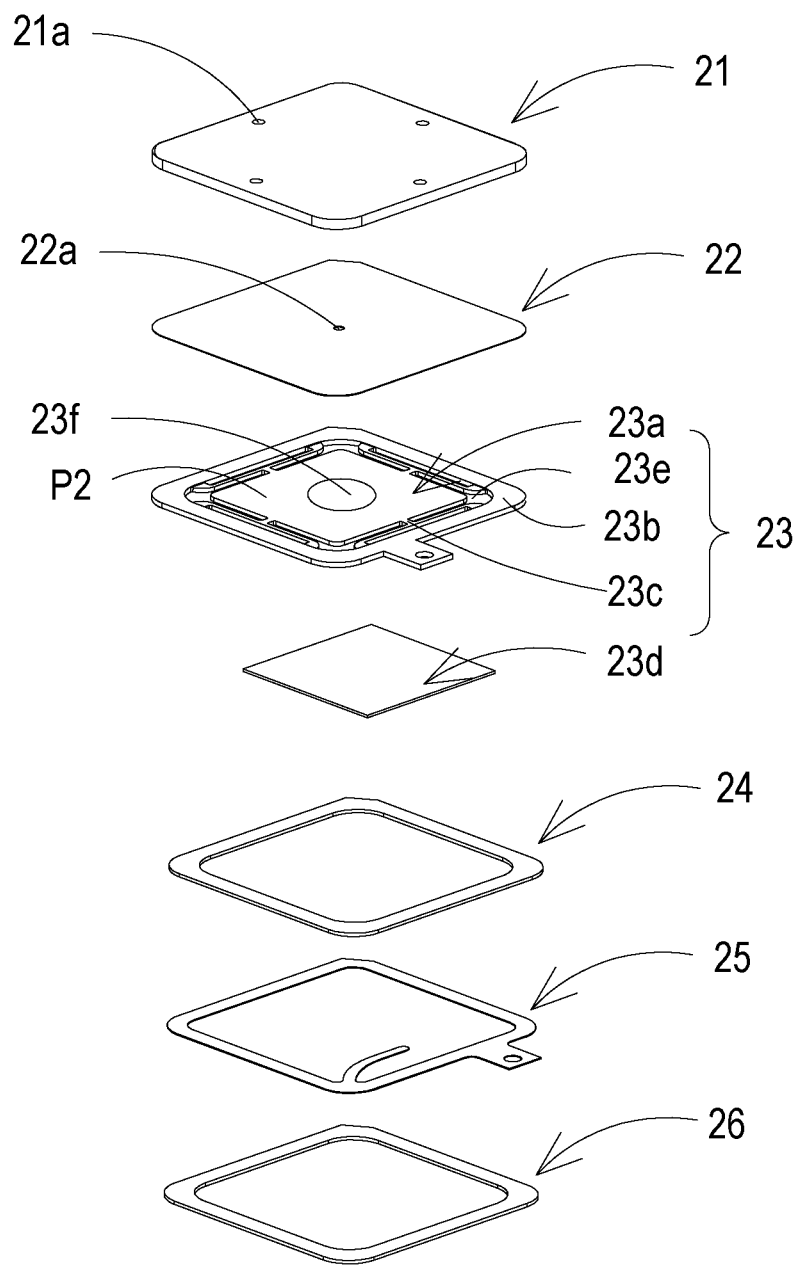
FIGS. 4A and 4B are exploded view illustrating the gas transporting actuator of the present disclosure taken along a first perspective and a second perspective, respectively.
Figure 4B:
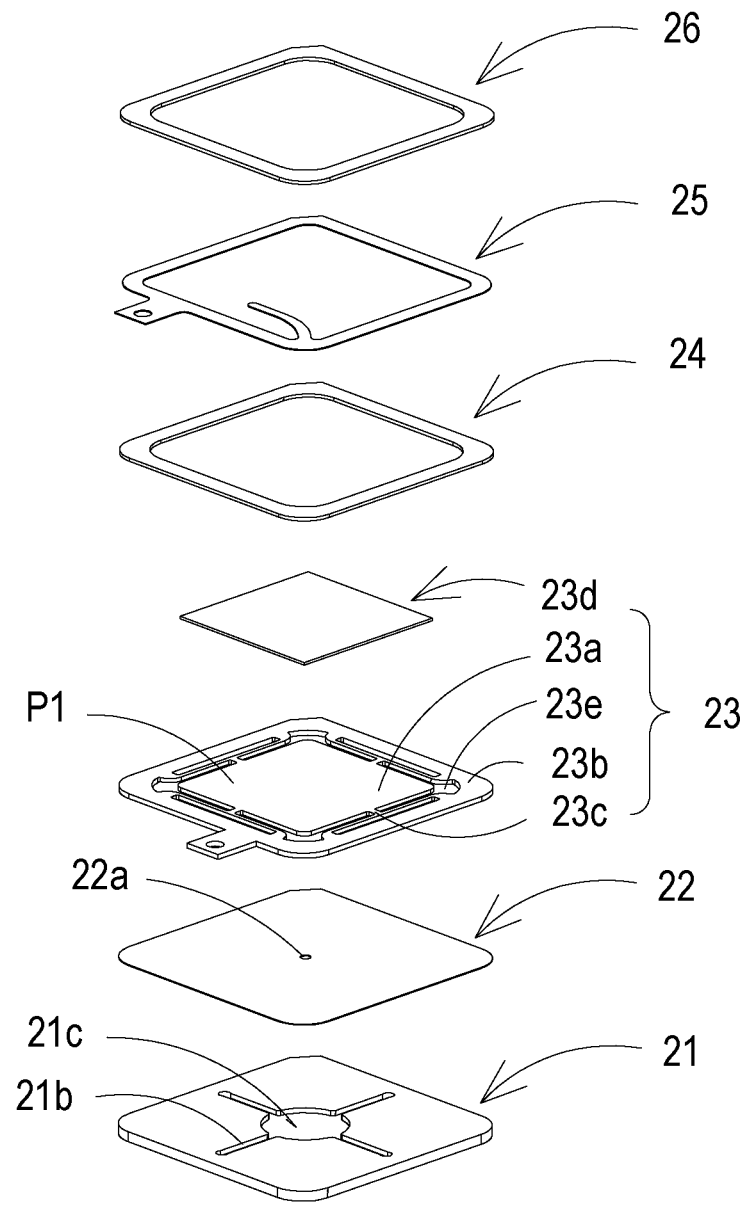
Figure 5A:
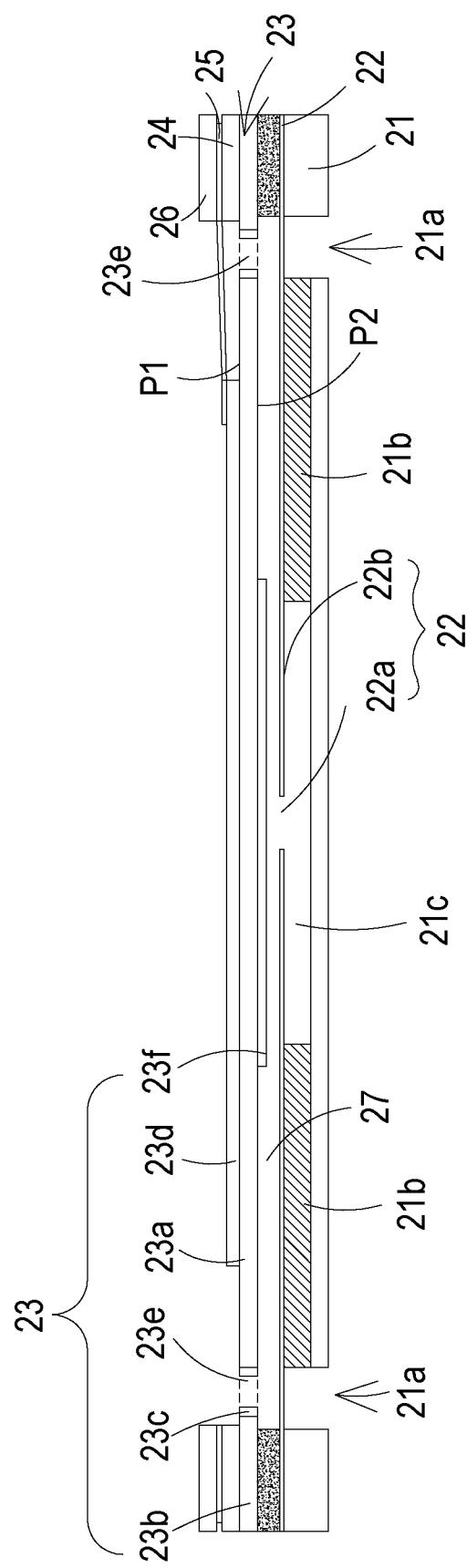
FIG. 5A is a schematic cross-sectional view illustrating the gas transporting actuator of FIG. 4A.
Figure 5B:
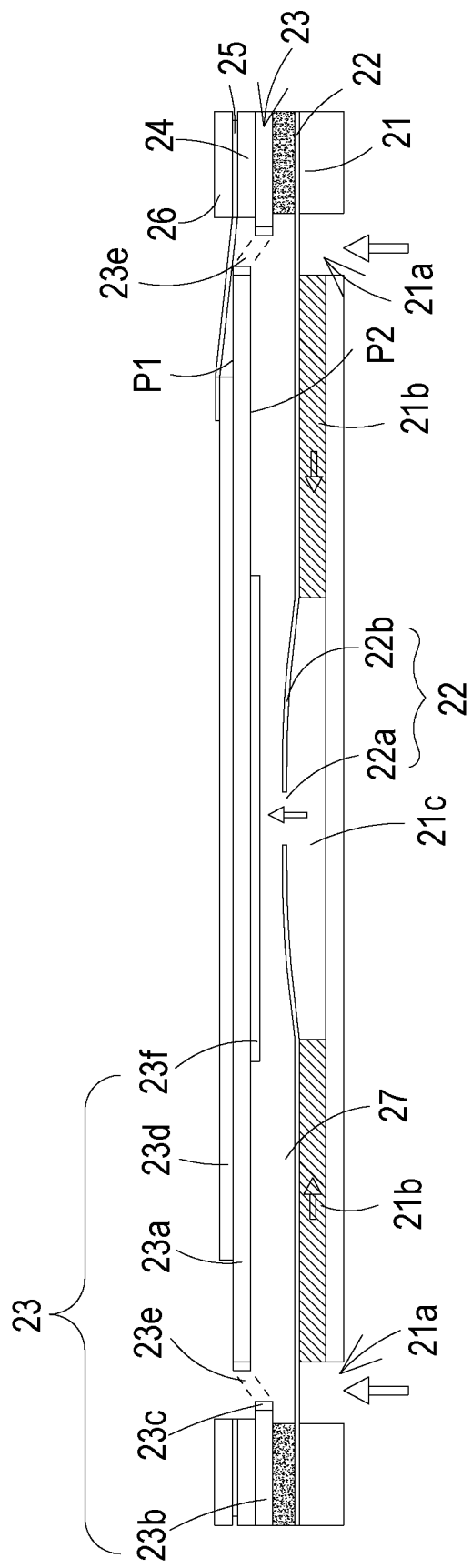
FIGS. 5B, 5C and 5D are schematic views illustrating actions of the gas transporting actuator of FIG. 4A.
Figure 5C:
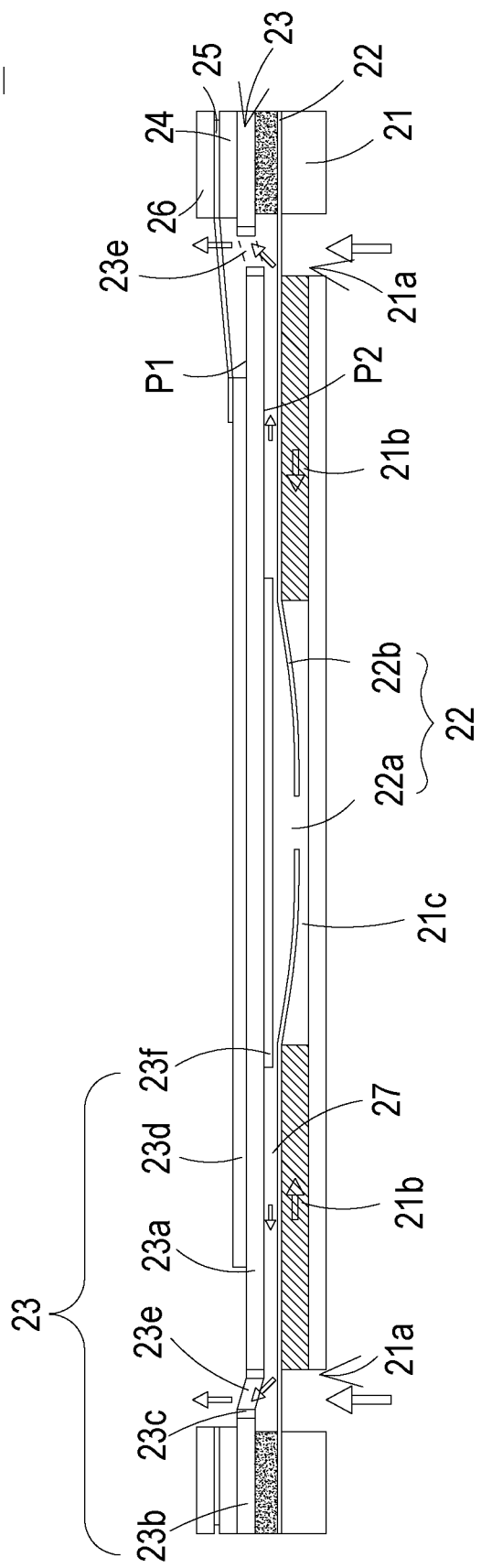
Figure 5D:
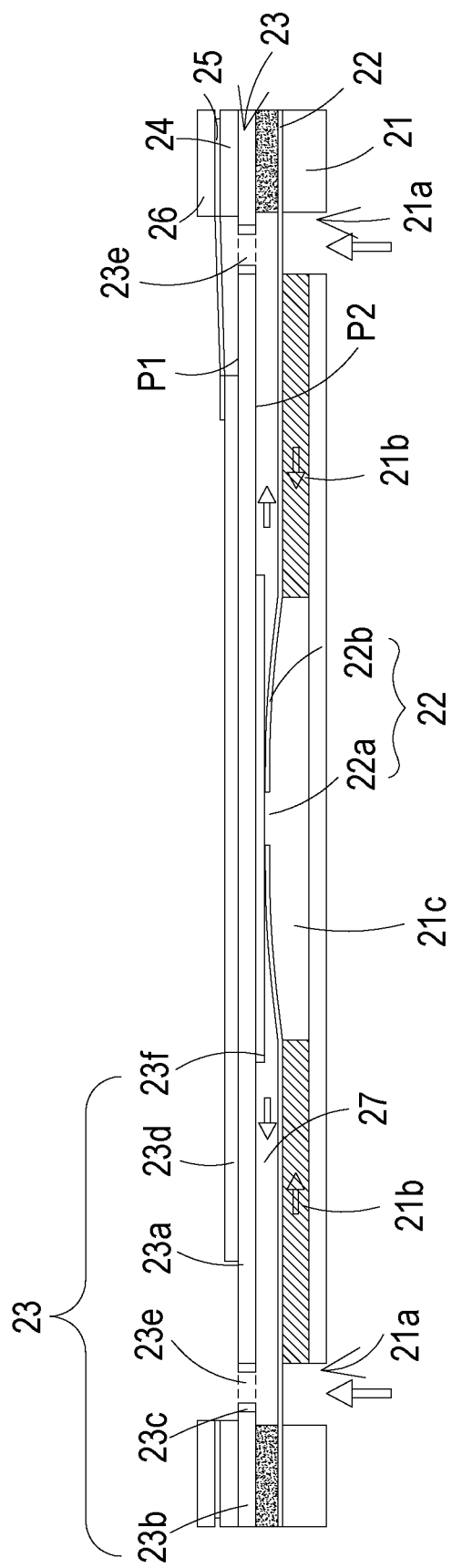

Please refer to FIGS. 3, 4A, 4B and 5A to 5D. FIGS. 4A and 4B are exploded view illustrating the gas transporting actuator of the present disclosure taken along a first perspective and a second perspective, respectively. FIG. 5A is a schematic cross-sectional view illustrating the gas transporting actuator of FIG. 4A. FIGS. 5B, 5C and 5D are schematic views illustrating actions of the gas transporting actuator of FIG. 4A. In the embodiment, the gas transporting actuator 2 includes a gas inlet plate 21, a resonance plate 22, a piezoelectric actuator 23, a first insulation plate 24, a conducting plate 25 and a second insulation plate 26, which are stacked and assembled sequentially. Two opposite lateral sides of the gas transporting actuator 2 abut two of the partition plates 15, respectively, or abut the partition plate 15 and an inner wall of the casing 1, respectively. The gas transporting actuator 2 may connect to the partition plate 15 and the inner wall of the casing 1 directly, via a connecting part, or any other suitable manner, and thus be fastened in the branch channel 13, as shown in FIG. 3. The gas inlet plate 21 is located at the junction between the airflow chamber 11 and the branch channels 13, and has at least one inlet aperture 21a, at least one convergence channel 21b and a convergence chamber 21c. The convergence channel 21b is aligned with and in communication with the inlet aperture 21a. In the embodiment, the numbers of the inlet apertures 21a and the convergence channels 21b are four, respectively, but not limited thereto. The convergence channel 21b has an end in fluid communication with the corresponding inlet aperture 21a and another end in fluid communication with the convergence chamber 21c. The inlet aperture 21a allows the air to flow in and the convergence channel 21b guides the air from the inlet aperture 21a toward the convergence chamber 21c. The resonance plate 22 has a central aperture 22a and a movable part 22b. The central aperture 22a is vertically aligned with the convergence chamber 21c. The movable part 22b surrounds the central aperture 22a. The piezoelectric actuator 23 is aligned with the resonance plate 22 and includes a suspension plate 23a, an outer frame 23b, at least one connection component 23c and a piezoelectric element 23d. The outer frame 23b is arranged around the suspension plate 23a. The connection component 23c is connected between the outer frame 23b and the suspension plate 23a for elastically supporting the suspension plate 23a. Moreover, at least one vacant space 23e is formed among the connection components 23c, the outer frame 23b and the suspension plate 23a. The suspension plate 23a has a first surface P1 and a second surface P2. The piezoelectric element 23d is attached on the first surface P1 of the suspension plate 23a and has a square structure. A length of a side of the piezoelectric element 23d is smaller than or equal to a length of a side of the suspension plate 23a. The suspension plate 23a has a bulge 23f disposed on the second surface P2 thereof. The suspension plate 23a of the piezoelectric element 23 is disposed separately from the resonance plate 22 through the outlet frame 23b to form a chamber 27 between the suspension plate 23a of the piezoelectric actuator 23, the outlet frame 23b and the resonance plate 22. In addition, the first insulation plate 24, the conducting plate 25 and the second insulation plate 26 are stacked sequentially on the piezoelectric actuator 23.

As shown in FIG. 5B, when the piezoelectric element 23d of the piezoelectric actuator 23 is actuated by an applied voltage, the piezoelectric element 23d is deformed by the piezoelectric effect, and the suspension plate 23a is driven to vibrate upwardly. Thereby, the movable part 22b of the resonance plate 22 is simultaneously driven to vibrate upwardly due to the Helmholtz resonance effect. Since the moveable part 22b vibrates upwardly, the volume of the convergence chamber 21c is expended and the air is inhaled into the convergence chamber 21c through the inlet aperture 21a. Please refer to FIG. 5C. The gas transporting actuator 2 is continuously actuated and the suspension plate 23a of the piezoelectric actuator 23 vibrates downwardly. Thereby, the movable part 22b of the resonance plate 22 is simultaneously driven to vibrate downwardly and the volume of the convergence chamber 21c is shrunken. The air is transported from the convergence chamber 21c to the chamber 27 formed between the piezoelectric actuator 23 and the resonance plate 22, pushed to the periphery by the bulge 23f of the suspension plate 23a, and discharged out through the vacant space 23e. Finally, as shown in FIG. 5D, the suspension plate 23a vibrates upwardly to the initial position and the volume of the chamber 27 is shrunken while the movable part 22b of the resonance plate 22 is displaced upwardly. The air is discharged through the periphery and the vacant space 23e. Since the volume of the convergence chamber 21c is expanded again, the air is inhaled through the inlet aperture 21a continuously. Repeating the above actions, the air is inhaled through the inlet aperture 21a and discharged through the vacant space 23e to achieve the gas transportation.

Figure 6:
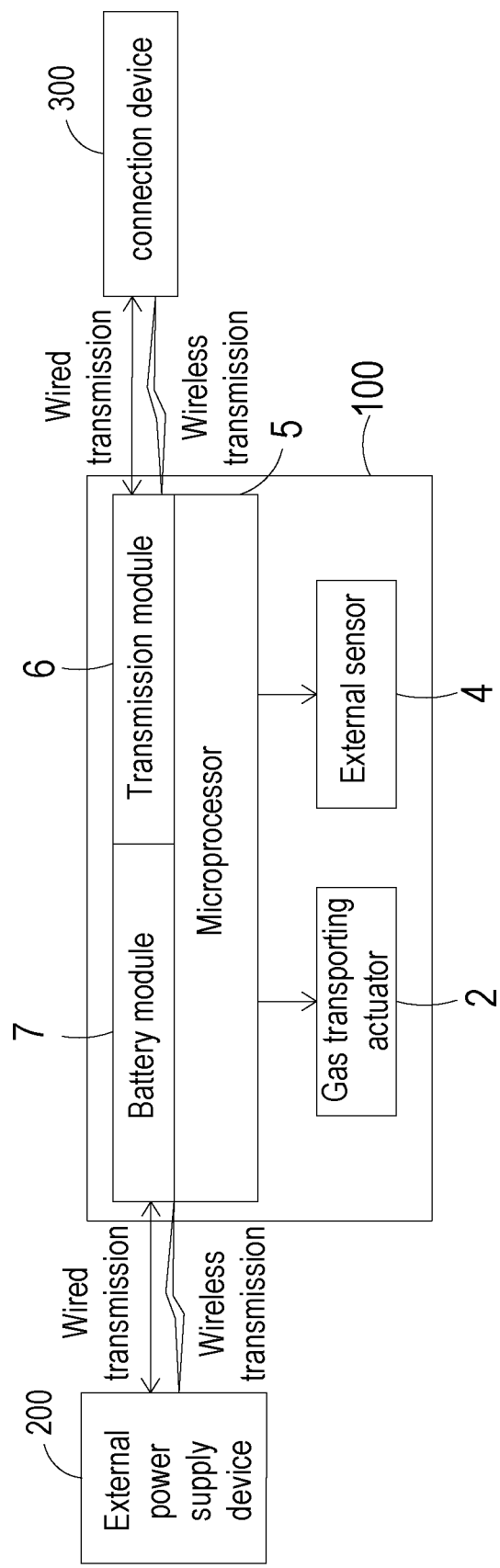
FIG. 6 is a block diagram of the gas detecting device of the present disclosure.

Please refer to FIGS. 2 and 6. The gas detecting device 100 further includes a microprocessor 5, a transmission module 6 and a battery module 7. The microprocessor 5 is electrically connected to the battery module 7, the transmission module 6, the gas transporting actuator 2 and the valve 3 to control the actuation of the gas transporting actuator 2. The external sensor 4 is assembled in the connection channel 14, and is electrically connected to and in data communication with the microprocessor 5. Therefore, detected results from the sensor of the external sensor 4 can be analyzed, calculated, stored and converted into detected values by the microprocessor 5. When the microprocessor 5 actuates the gas transporting actuator 2, the gas transporting actuator 2 starts to inhale the air and transport the air into the branch channel 13 and the connection channel 14. In that, the sensor of the external sensor 4 disposed in the connection channel 14 starts to measure the air contained in the connection channel 14 and transmit the detected results to the microprocessor 5. The detected results are analyzed and converted into the detected values by the microprocessor 5 and the detected values are stored in the microprocessor 5. The detected values stored in the microprocessor 5 are transmitted to a connection device 300 via the transmission module 6, so that information carried by the detected values are displayed, stored and transmitted through the connection device 300 and a notification alert is issued. The connection device 300 can be at least one selected from the group consisting of a cloud system, a portable device, a computer system, a display device and combinations thereof.

In addition, the transmission module 6 can be at least one selected from the group consisting of a wired transmission module and a wireless transmission module, so as to achieve the transmission with the connection device 300. In an embodiment, the transmission module 6 can be the wired transmission module and selected from the group consisting of a USB transmission module, a mini-USB transmission module, a micro-USB transmission module and combinations thereof. In another embodiment, the transmission module 6 can be the wireless transmission module and selected from the group consisting of a Wi-Fi transmission module, a Bluetooth transmission module, a radio frequency identification transmission module, a near field communication transmission module and combinations thereof.

As mentioned above, the battery module 7 is used to provide the electrical energy to the microprocessor 5 to control the gas transporting actuator 2, the transmission module 6, the valve 3 and the sensor of the external sensor 4 to be actuated. Moreover, the battery module 7 is electrically connected to an external power supply device 200 to receive and store electrical energy. The external power supply device 200 can transmit the electrical energy to the battery module 7 by means of a wired transmission technology or transmit the electrical energy to the battery module 7 by a wireless transmission technology, but not limited thereto.

Figure 7A:
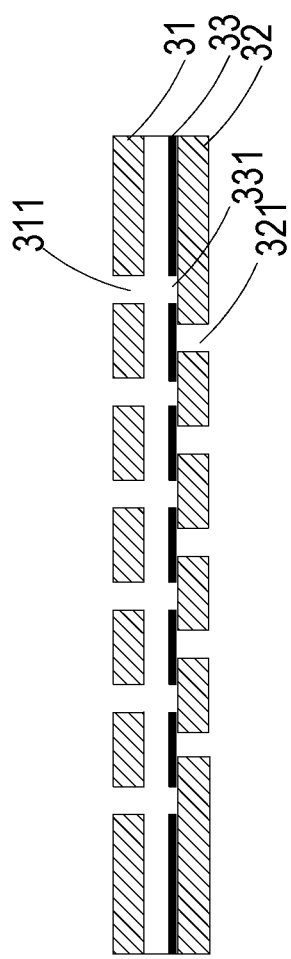
FIGS. 7A and 7B are schematic cross-sectional views illustrating the actions of the valve used in the gas detecting device according to an embodiment of the present disclosure.

Please refer to FIGS. 2 and 7A. In the embodiment, the valve 3 includes a stationary component 31, a sealing component 32 and a displacement component 33. The displacement component 33 is disposed between the stationary component 31 and the sealing component 32. The stationary component 31 has a plurality of first orifices 311. The displacement component 33 has a plurality of second orifices 331 respectively corresponding in position to the plurality of first orifices 311 of the stationary component 31. That is, the plurality of first orifices 311 of the stationary component 31 are aligned with the plurality of second orifices 331 of the displacement component 33. The sealing component 32 has a plurality of third orifices 321. The plurality of third orifices 321 of the sealing component 32 are misaligned with the plurality of first orifices 311 of the stationary component 31.

Figure 7B:
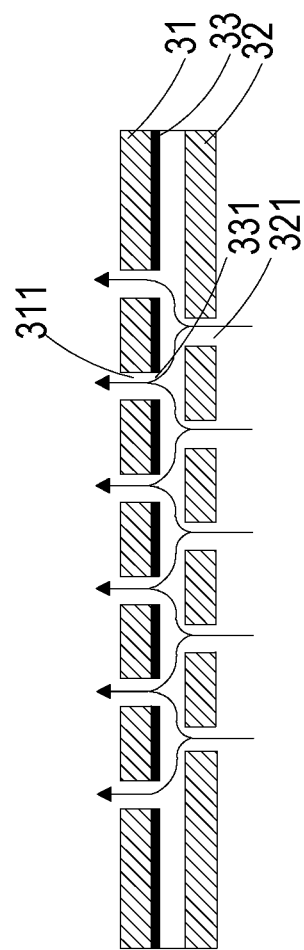

Please refer to FIGS. 7A and 6. In a first aspect of the valve 3 in the present disclosure, the displacement component 33 is made of a charged material, and the stationary component 31 is made of a bipolar conductive material. In case that the displacement component 33 and the stationary component 31 are controlled by the microprocessor 5 to maintain in the same polarity, the displacement component 33 moves toward the sealing component 32 so that the valve 3 is in a closed state. Please refer to FIG. 7B. The displacement component 33 is made of a charged material, and the stationary component 31 is made of a bipolar conductive material. In case that the displacement component 33 and the stationary component 31 are controlled by the microprocessor 5 to maintain in opposite polarity, the displacement component 33 moves toward the stationary component 31 so that the valve 3 is in an open state. According to the above descriptions, it is understood that by adjusting the polarity of the stationary component 31, the displacement member 33 is moved to switch the valve 3 between the open state and the closed state. Since the microprocessor 5 is electrically connected to the valve 3, the polarity of the stationary component 31 can be controlled by the microprocessor 5.

In a second aspect of the valve 3 in the present disclosure, the displacement component 33 is made of a magnetic material, and the stationary component 31 is made of an electromagnet material and can be controlled to change its magnetic polarity. When the displacement component 33 and the stationary component 31 are controlled by the microprocessor 5 to maintain in the same polarity, the displacement component 33 moves toward the sealing component 32 so that the valve 3 is in the closed state. Alternatively, when the displacement component 33 and the stationary component 31 are controlled by the microprocessor 5 to maintain in opposite polarity, the displacement component 33 moves toward the stationary component 31 so that the valve 3 is in the open state. According to the above descriptions, it is understood that by adjusting the polarity of the stationary component 31, the displacement member 33 is moved to switch the valve 3 between the open state and the closed state. The polarity of the stationary component 31 can be controlled by the microprocessor 5.

In summary, the present disclosure provides a gas detecting device. By separately setting a plurality of gas transporting actuators in the different branch channels of the gas detecting device, the air contained in the airflow chamber is transported into the branch channel and the connection channel, so that the external sensor in the connection channel can detect the air flowing into the connection channel and obtain the air quality information. The external sensor is detachably assembled in the connection channel, so that the user can easily replace the required sensor according to the particle requirements.

While the disclosure has been described in terms of what is presently considered to be the most practical and preferred embodiments, it is to be understood that the disclosure needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A gas detecting device comprising:
a casing having an airflow chamber, at least one inlet, at least one branch channel and at least one connection channel, wherein the airflow chamber is in fluid communication with an environment outside the casing through the at least one inlet, the at least one branch channel is in fluid communication with the airflow chamber, and the at least one connection channel is in fluid communication with the at least one branch channel;
at least one gas transporting actuator disposed in the at least one branch channel and having a gas inlet plate, a resonance plate and a piezoelectric actuator, wherein the gas transporting actuator is actuated to inhale air into the airflow chamber through the at least one inlet and transport the air into the at least one branch channel;
at least one valve disposed between the at least one connection channel and the at least one branch channel to control the air to flow into the at least one connection channel; and
at least one external sensor detachably assembled in the at least one connection channel and comprising a sensor to measure the air in the at least one connection channel.

2. The gas detecting device according to claim 1, wherein the gas inlet plate has at least one inlet aperture, at least one convergence channel and a convergence chamber, wherein the at least one convergence channel is aligned with the at least one inlet aperture, and the at least one inlet aperture allows the air to flow in and the convergence channel guides the air from the inlet aperture toward the convergence chamber, wherein the resonance plate has a central aperture and a movable part, the central aperture is aligned with the convergence chamber, the movable part surrounds the central aperture, and the piezoelectric actuator is aligned with the resonance plate, wherein a chamber is formed between the resonance plate and the piezoelectric actuator, so that the air from the at least one inlet aperture of the gas inlet plate is converged to the convergence chamber along the at least one convergence channel and flows into the chamber through the central aperture of the resonance plate when the piezoelectric actuator is driven, whereby the air is further transported through a resonance between the piezoelectric actuator and the movable part of the resonance plate.

3. The gas detecting device according to claim 2, wherein the piezoelectric actuator comprises:
a suspension plate having a first surface and a second surface, wherein the suspension plate is permitted to undergo a bending vibration;
an outer frame arranged around the suspension plate;
at least one connection component connected between the suspension plate and the outer frame for elastically supporting the suspension plate; and
a piezoelectric element, wherein a length of a side of the piezoelectric element is smaller than or equal to a length of a side of the suspension plate, and the piezoelectric element is attached on the first surface of the suspension plate to drive the suspension plate to undergo the bending vibration in response to an applied voltage.

4. The gas detecting device according to claim 2, wherein the gas transporting actuator comprises a conducting plate, a first insulation plate and a second insulation plate, and the gas inlet plate, the resonance plate, the piezoelectric actuator, the first insulation plate, the conducting plate and the second insulation plate are stacked and assembled sequentially.

5. The gas detecting device according to claim 1, further comprising a microprocessor and a transmission module, wherein the microprocessor is used to control the transmission module, the gas transporting actuator and the valve to be actuated, and the sensor of the external sensor assembled in the connection channel is electrically connected to and in data communication with the microprocessor, wherein detected results from the sensor are analyzed and converted into detected values by the microprocessor, and the transmission module transmits the detected values to a connection device so that information carried by the detected values are displayed, stored and transmitted through the connection device and a notification alert is issued.

6. The gas detecting device according to claim 5, wherein the connection device is at least one selected from the group consisting of a cloud system, a portable device, a computer system and combinations thereof.

7. The gas detecting device according to claim 1, wherein the sensor of the external sensor is at least one selected from the group consisting of an oxygen sensor, a carbon monoxide sensor, a carbon dioxide sensor, a temperature sensor, a humidity sensor and combinations thereof.

8. The gas detecting device according to claim 1, wherein the sensor of the external sensor is a volatile organic compound sensor.

9. The gas detecting device according to claim 1, wherein the sensor of the external sensor is at least one selected from the group consisting of a bacterial sensor, a virus sensor, a microorganism sensor and combinations thereof.

10. The gas detecting device according to claim 5, wherein the valve comprises a stationary component, a sealing component and a displacement component, wherein the displacement component is disposed between the stationary component and the sealing component, the stationary component has a plurality of first orifices, the displacement component has a plurality of second orifices, and the sealing component has a plurality of third orifices, wherein the plurality of the first orifices of the stationary component are aligned with the plurality of the second orifices of the displacement component, and the plurality of the third orifices of the sealing component are misaligned with the plurality of the first orifices of the stationary component, wherein the displacement component is controlled to move toward the stationary component by the microprocessor so that the valve is in an open state.

11. A gas detecting device comprising:
at least one casing having at least one airflow chamber, at least one inlet, at least one branch channel and at least one connection channel, wherein the airflow chamber is in fluid communication with an environment outside the casing through the inlet, the at least one branch channel is in fluid communication with the airflow chamber, and the at least one connection channel is in fluid communication with the at least one branch channel;

at least one gas transporting actuator disposed on the at least one branch channel and having at least one gas inlet plate, at least one resonance plate and at least one piezoelectric actuator, wherein the gas transporting actuator is actuated to inhale air into the airflow chamber through the at least one inlet and transport the air into the branch channel;

at least one valve disposed between the at least one connection channel and the at least one branch channel to control the air to flow into the at least one connection channel; and at least one external sensor detachably assembled in the at least one connection channel and comprising at least one sensor to measure the air in the at least one connection channel.

* * * * *